(12) United States Patent
Philippe

(10) Patent No.: US 8,242,097 B2
(45) Date of Patent: Aug. 14, 2012

(54) COSMETIC USE OF POLYSACCHARIDE COMPOUNDS CONTAINING NON-POLYMER SILOXANE GRAFT(S)

(75) Inventor: Michel Philippe, Wissous (FR)

(73) Assignee: L'Oreal S.A., Paris (FR)

(*) Notice: Subject to any disclaimer, the term of this patent is extended or adjusted under 35 U.S.C. 154(b) by 1178 days.

(21) Appl. No.: 11/660,380

(22) PCT Filed: Aug. 18, 2005

(86) PCT No.: PCT/EP2005/009986
§ 371 (c)(1),
(2), (4) Date: Jul. 30, 2007

(87) PCT Pub. No.: WO2006/018323
PCT Pub. Date: Feb. 23, 2006

(65) Prior Publication Data
US 2007/0275927 A1 Nov. 29, 2007

Related U.S. Application Data

(60) Provisional application No. 60/612,176, filed on Sep. 23, 2004.

(30) Foreign Application Priority Data

Aug. 19, 2004 (FR) ...................... 04 08995

(51) Int. Cl.
*A61K 31/715* (2006.01)
*C07H 1/00* (2006.01)

(52) U.S. Cl. .............. 514/57; 514/54; 514/59; 514/60; 536/102; 536/104; 536/123.1

(58) Field of Classification Search .................. None
See application file for complete search history.

(56) References Cited

U.S. PATENT DOCUMENTS

| 6,066,727 | A | 5/2000 | Yamamoto et al. |
| 6,630,133 | B1 | 10/2003 | Dupuis |
| 2002/0197225 | A1 | 12/2002 | Giroud et al. |
| 2004/0102354 | A1 | 5/2004 | Fack et al. |

FOREIGN PATENT DOCUMENTS

| EP | 1 016 400 A1 | 7/2000 |
| EP | 1 084 695 A1 | 3/2001 |
| EP | 1 095 959 A2 | 5/2001 |
| EP | 1 240 888 A1 | 9/2002 |
| WO | WO 02/055053 | 7/2002 |

OTHER PUBLICATIONS

Xiaolin Cai et al., "Cellulose fiber/poly(ethylene-co-methacrylic acid) composites with ionic interphase," Composites: Part A, vol. 34, pp. 1075-1084 (2003).
Mekki Abdelmouleh et al., "Interaction of Silane Coupling Agents with Cellulose," Langmuir, vol. 18, pp. 3203-3208 (2002).
French Search Report for FR 0408995, dated May 3, 2005, Examiner R. Menidjel.

*Primary Examiner* — Elli Peselev
(74) *Attorney, Agent, or Firm* — O'Brien Jones PLLC

(57) ABSTRACT

The present disclosure relates to the cosmetic use of grafted polysaccharide compounds comprising at least one non-polymer siloxane graft that may be obtained by reacting a polysaccharide and a siloxane compound corresponding to formula (I), such as for the cosmetic treatment of keratin materials. The disclosure also relates to compositions comprising the grafted polysaccharide compounds in a cosmetically acceptable medium, and also to certain novel grafted polysaccharide compounds comprising at least one non-polymer siloxane graft.

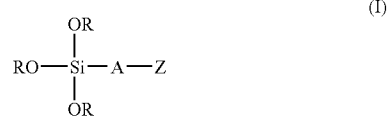

18 Claims, No Drawings

COSMETIC USE OF POLYSACCHARIDE COMPOUNDS CONTAINING NON-POLYMER SILOXANE GRAFT(S)

CROSS REFERENCE TO RELATED APPLICATIONS

This application is a national phase application based on PCT/EP2005/009986, filed Aug. 18, 2005, which claims the priority of French Patent Application No. 0408995, filed Aug. 19, 2004; and the benefit of U.S. Provisional Application No. 60/612,176, filed Sep. 23, 2004, the contents of all of which are incorporated herein by reference.

The present invention relates to the use of polysaccharide compounds containing non-polymer siloxane graft(s) in cosmetics, and to compositions comprising them, and also to novel polysaccharide compounds containing non-polymer siloxane graft(s).

In the cosmetics field, it is especially sought to improve the cosmetic properties of keratin materials, such as the hair and the skin, and more particularly sensitized hair, i.e. hair that has become damaged or embrittled, especially due to the chemical action of atmospheric agents and/or of hair treatments such as permanent-waving, dyeing or bleaching.

With this aim, it is common practice to use complementary cosmetic agents known as conditioning agents, for example cationic polymers or silicones, which are intended mainly to repair or limit the harmful or undesirable effects induced by the various treatments or attacking factors to which hair fibres are more or less repeatedly subjected. These conditioning agents also improve the cosmetic behavior of natural hair.

Other conditioning agents, such as the amphoteric polysaccharides described in document U.S. Pat. No. 6,066,727 may be used in cosmetic hair compositions.

However, these conditioning agents are not always very efficient as regards conditioning and remanence of cosmetic properties. After several uses, the hair becomes laden and lacks lightness and suppleness.

The Applicant has found, surprisingly and unexpectedly, that the use of polysaccharide compounds containing non-polymer siloxane graft(s) in cosmetics, makes it possible to overcome the drawbacks described above and to obtain excellent cosmetic properties such as an excellent conditioning and protecting effect on the hair, good disentangling of the hair, softness and a smoothing effect on keratin fibres.

Such compounds and the process for preparing them are described in the article "Cellulose fiber/poly(ethylene-co-methacrylic acid) composites with ionic interphase" de Xiaolin Cai et al, Composites Part A 34, 2003, pages 1075-1084.

In addition, the use of these polysaccharide compounds containing non-polymer siloxane graft(s) leads to good remanence of these properties, even after washing the hair several times, without observing an excessive deposit that would lead to laden, non-maleable and non-supple hair.

These conditioning agents also give the skin cosmetic properties such as good moisturization.

One subject of the present invention is thus the use of polysaccharide compounds containing non-polymer siloxane graft(s) as described below in cosmetics, especially for the cosmetic treatment of keratin materials, such as caring for and protecting the hair, hairstyling, permanent-waving, relaxing, dyeing or bleaching the hair, or alternatively cleansing and care of the skin.

Another subject of the invention is a cosmetic composition comprising at least one polysaccharide compound containing non-polymer siloxane graft(s) as described below, in a cosmetically acceptable medium.

A subject of the invention is also novel compounds as described below.

Other subjects, characteristics, aspects and advantages of the invention will emerge even more clearly on reading the description and the various examples that follow.

The polysaccharide compounds containing non-polymer siloxane graft(s) used according to the invention may be obtained by reaction of a polysaccharide and a siloxane compound corresponding to formula (I):

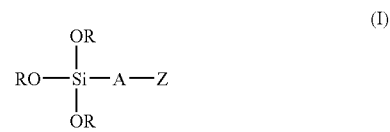

in which:
- R represents a linear or branched $C_1$-$C_{12}$ and preferably $C_1$-$C_8$ alkyl group, or a linear or branched $C_2$-$C_8$ alkenyl group,
- A represents a linear or branched, saturated or unsaturated, optionally hydroxylated $C_1$-$C_{22}$ divalent hydrocarbon-based group, which may contain a hetero atom N, O or S in the chain,
- Z represents —$NHR_4$, —$^+NR_1R_2R_3X^-$, —$C\equiv N$, —SH, —OH, a guanidine group or guanidinium salt, or a sulfonate, sulfate, phosphate or phosphonate salt, the salts possibly being organic or mineral, $Cl^-$ being preferred as anion and $Na^+$ being preferred as cation,
- $R_4$ represents a hydrogen atom or a linear or branched $C_1$-$C_{22}$ and preferably $C_1$-$C_{18}$ alkyl group, optionally bearing at least one hydroxyl and/or quaternary ammonium substituent,
- $R_1$, $R_2$ and $R_3$ represent, independently of each other, a hydrogen atom or a linear or branched $C_1$-$C_{22}$ and preferably $C_1$-$C_{18}$ alkyl group, optionally bearing at least one hydroxyl substituent, and
- X represents a mineral or organic anion, for example a halogen atom such as a bromine or chlorine atom, the chlorine atom being particularly preferred, or an acetate, a citrate, a lactate, an oleate or a behenate.

The polysaccharide is preferably a cellulose, a hemicellulose, a lignocellulose, a starch, an inulin, a guar gum, a xanthan gum, a pullulan, an agar-agar, a sodium, potassium or ammonium alginate, a carrageenan, a dextran, a furcellaran, a gellan gum, a gum arabic, a gum tragacanth, a hyaluronic acid, a konjac mannan, a lignin sulfonate, a carob gum, a partially N-acetylated chitin, a pectin, a polydextrose, a rhamsan gum or a welan gum.

More preferably, the polysaccharide is a cellulose, a hemicellulose, a carboxymethylcellulose, a hydroxyethylcellulose, a hydroxypropylcellulose, a hydroxypropylmethylcellulose, a methylcellulose, a lignocellulose, a starch, a starch acetate, a hydroxyethyl starch, a hydroxypropyl starch, an inulin, a guar gum, a carboxymethylguar gum, a carboxymethylhydroxypropylguar gum, a hydroxyethylguar gum, a hydroxypropylguar gum or a xanthan gum.

The polysaccharide preferably has a weight-average molecular mass between 500 and 15 000 000 and better still between 1000 and 10 000 000.

As examples of linear or branched $C_1$-$C_{12}$, preferably $C_1$-$C_8$ and even more preferably $C_1$-$C_4$ alkyl groups, mention may be made especially of methyl, ethyl, n-propyl, isopropyl, n-butyl and tert-butyl groups.

As examples of linear or branched $C_2$-$C_8$ and preferably $C_2$-$C_4$ alkenyl groups, mention may be made especially of vinyl, allyl, crotonyl, butenyl, isobutenyl and tert-butenyl groups.

Examples of linear or branched, saturated or unsaturated $C_1$-$C_{22}$, preferably $C_1$-$C_{18}$ and better still $C_1$-$C_8$ divalent hydrocarbon-based groups that may especially be mentioned include linear or branched alkylene groups, such as methylene, ethylene, n-propylene, isopropylene, n-butylene, tert-butylene, hexylene or octylene groups; linear or branched $C_2$-$C_8$ alkylene groups, such as vinylene, allylene, crotonylene, butenylene, isobutenylene, tert-butenylene, hexenylene or octenylene. These groups may also bear at least one hydroxyl substituent and/or may comprise an N, O or S hetero atom in the chain.

Examples of $C_1$-$C_{22}$ and preferably $C_1$-$C_{18}$ alkyl groups that may especially be mentioned include linear or branched $C_1$-$C_4$ alkyl groups, such as methyl, ethyl, n-propyl, isopropyl, n-butyl or tert-butyl groups, and linear or branched $C_{12}$-$C_{18}$ alkyl groups, such as lauryl, myristyl, cetyl or stearyl groups.

The amphoteric polysaccharide compounds containing non-polymer siloxane graft(s) that are most particularly preferred in the invention are those obtained by reaction:

of a polysaccharide chosen from a cellulose, a hemicellulose, a carboxymethylcellulose, a hydroxyethylcellulose, a hydroxypropylcellulose, a hydroxypropylmethylcellulose, a methylcellulose, a lignocellulose, a starch, a starch acetate, a hydroxyethyl starch, a hydroxypropyl starch, an inulin, a guar gum, a carboxymethylguar gum, a carboxymethylhydroxypropylguar gum, a hydroxyethylguar gum, a hydroxypropylguar gum and a xanthan gum; and of a of a siloxane compound corresponding to formula (I):

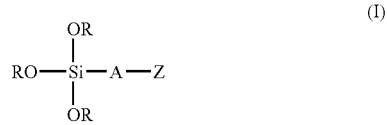

(I)

in which:

R represents a linear or branched $C_1$-$C_4$ alkyl group, such as methyl, ethyl, n-propyl, isopropyl, n-butyl or tert-butyl, or a linear or branched $C_2$-$C_4$ alkenyl group, such as vinyl, allyl, crotonyl, butenyl, isobutenyl or tert-butenyl, A represents a linear or branched, saturated or unsaturated, optionally hydroxylated $C_1$-$C_{18}$ divalent hydrocarbon-based group, which may contain an N, O or S hetero atom in the chain, such as methylene, ethylene, n-propylene, isopropylene, n-butylene, tert-butylene, hexylene, octylene, dodecylene, hexadecylene or octadecylene or a linear or branched $C_2$-$C_8$ alkenylene group, such as vinylene, allylene, crotonylene, butenylene, isobutenylene, tert-butenylene, hexenylene or octenylene, Z represents —$NHR_4$, —$^+NR_1R_2R_3X^-$, —C≡N, —SH, —OH, a guanidine group or guanidinium salt, or a sulfonate, sulfate, phosphate or phosphonate salt, the salts possibly being organic or mineral, $Cl^-$ being preferred as anion and $Na^+$ being preferred as cation, $R_4$ represents a hydrogen atom or a linear or branched $C_1$-$C_4$ alkyl group, such as methyl, ethyl, n-propyl, isopropyl, n-butyl or tert-butyl, or a linear or branched $C_{12}$-$C_{18}$ alkyl group, such as lauryl, myristyl, cetyl or stearyl, optionally bearing at least one hydroxyl and/or quaternary ammonium substituent, $R_1$, $R_2$ and $R_3$ represent, independently of each other, a hydrogen atom or a linear or branched $C_1$-$C_4$ alkyl group, such as methyl, ethyl, n-propyl, isopropyl, n-butyl or tert-butyl, or a linear or branched $C_{12}$-$C_{18}$ alkyl group, such as lauryl, myristyl, cetyl or stearyl, optionally bearing at least one hydroxyl substituent, and X represents a halogen atom, an acetate, a citrate, a lactate, an oleate or a behenate.

The amphoteric polysaccharide compounds according to the invention may be prepared via the process described in "Interaction of silane coupling agents with cellulose", American Chemical Society, Langmuir 2002, 18, 3203-3208, or via the process described in "Cellulose fiber/poly(ethylene-comethacrylic acid) composites with ionic interphase" de Xiaolin Cai et al, Composites Part A 34, 2003, pages 1075-1084.

The polysaccharide compounds containing non-polymer siloxane graft(s) as described above are used in cosmetics, and especially for the cosmetic treatment of keratin materials, such as caring for and protecting the hair, as a conditioning agent for hold and discipline of the hairstyle, as a fixing agent; but also for cleansing and caring for the skin and for making up the skin, the lips and the nails.

A subject of the present invention is also a cosmetic composition comprising, in a cosmetically acceptable medium, at least one polysaccharide compound containing non-polymer siloxane graft(s) as described above, preferably in an amount ranging from 0.05% to 50% by weight and better still from 0.5% to 25% by weight relative to the total weight of the composition.

The term "cosmetically acceptable medium" means a medium that is compatible with any keratin material, such as the skin, the hair, the nails, the eyelashes, the eyebrows and the lips and any other area of body or facial skin.

The cosmetically acceptable medium may consist solely of water or of a mixture of water and of a cosmetically acceptable solvent such as a $C_1$-$C_4$ lower alcohol, such as ethanol, isopropanol, tert-butanol or n-butanol; alkylene polyols, for instance propylene glycol; polyol ethers; and mixtures thereof.

The composition according to the invention may also comprise one or more standard additives that are well known in the art, such as anionic, cationic, nonionic, amphoteric or zwitterionic surfactants, anionic, cationic, nonionic, amphoteric or zwitterionic polymers, thickeners, nacreous agents, opacifiers, UV-screening agents, fragrances, mineral, plant and/or synthetic oils, fatty acid esters, dyes, volatile or nonvolatile, organomodified or non-organomodified, cyclic or acyclic, branched or unbranched silicones, mineral or organic, natural or synthetic particles, preserving agents and pH stabilizers.

A person skilled in the art will take care to select the optional additives and the amount thereof such that they do not harm the properties of the compositions of the present invention.

These additives are generally present in the composition according to the invention in an amount ranging from 0 to 20% by weight relative to the total weight of the composition.

The cosmetic compositions in accordance with the invention may be in the form of a mousse, a gel, a spray or a lacquer and may be used in rinse-out or leave-in application.

The compositions in accordance with the invention may be used as hair products, especially rinse-out or leave-in products, and in particular for washing, caring for and/or conditioning the hair, holding the hairstyle, and shaping, dyeing, bleaching, permanently reshaping or relaxing the hair.

The compositions of the invention may also be used as care or hygiene products such as protective, treating or care creams for the face, the hands or the body, protective or care body milks, gels or mousses for caring for or cleansing the skin, or alternatively as products for making up or for removing makeup from the skin, the lips, the nails and the eyelashes.

Another subject of the present invention consists of novel polysaccharide compounds containing non-polymer siloxane graft(s) obtained by reaction of polysaccharide P' with a siloxane compound of formula (I) as described above.

P' represents a polysaccharide chain chosen from a hemicellulose, a lignocellulose, a starch, an inulin, a guar gum, a xanthan gum, a pullulan, an agar-agar, a sodium, potassium or ammonium alginate, a carrageenan, a dextran, a furcellaran, a gellan gum, a gum arabic, a gum tragacanth, a hyaluronic acid, a konjac mannan, a lignin sulfonate, a carob gum, a partially N-acetylated chitin, a pectin, a polydextrose, a rhamsan gum and a welan gum, preferably having a weight-average molecular mass of between 500 and 15 000 000 and better still between 1000 and 10 000 000.

More preferably, the polysaccharide chain is a hemicellulose, a carboxymethylcellulose, a hydroxyethylcellulose, a hydroxypropylcellulose, a hydroxypropylmethylcellulose, a methylcellulose, a lignocellulose, a starch, a starch acetate, a hydroxyethyl starch, a hydroxypropyl starch, an inulin, a guar gum, a carboxymethylguar gum, a carboxymethylhydroxypropylguar gum, a hydroxyethylguar gum, a hydroxypropylguar gum or a xanthan gum.

EXAMPLES

Example 1

20 g of hydroxyethylcellulose are dispersed in 480 ml of an 80/20 ethanol/water mixture, at room temperature. 15.93 g of aminopropyltriethoxysilane (APTES) diluted in 50 ml of an 80/20 ethanol/water mixture are introduced.

The mixture is stirred for 2 hours at room temperature. The precipitate is isolated by centrifugation and is dried in an oven under vacuum at 40° C.

The product is then heated at 110° C. under an argon atmosphere for 2 hours. 14.5 g of a yellow powder are thus obtained.

Example 2

20 g of hydroxyethylcellulose are dispersed in 480 ml of an 80/20 ethanol/water mixture, at room temperature. 15.93 g of aminopropyltriethoxysilane (APTES) diluted in 50 ml of an 80/20 ethanol/water mixture are introduced.

The mixture is stirred for 2 hours at room temperature. The precipitate is isolated by centrifugation and is dried in an oven under vacuum at 40° C.

The product is then heated at 110° C. under a vacuum of 263 Pa (2 mmHg) for 2 hours. 14 g of a yellow powder are thus obtained.

Example 3

Shampoo

A shampoo was prepared using the following ingredients, the amounts of which are given as weight percentages of active material relative to the total weight of the composition:

| | |
|---|---|
| Sodium lauryl ether sulfate (Texapon N702 from Cognis) | 12.5% |
| Cocoylbetaïne (Dehyton AB 30 from Goldschmidt) | 2.5% |
| Dimethicone (DC200 Fluid from Dow Corning) | 2.0% |
| Compound of Example 1 | 0.5% |
| Cocamide monoisopropanolamine | 0.4% |
| Carbomer | 0.2% |
| Preserving agent | qs |
| Fragrance | qs |
| Citric acid/sodium hydroxide qs | pH 6.5 |
| Water qs | 100 |

Example 4

Conditioner

A conditioner was prepared using the following ingredients, the amounts of which are given as weight percentages of active material relative to the total weight of the composition:

| | |
|---|---|
| Behenyltrimethylammonium chloride (Genamin KDMP from Clariant) | 1.2% |
| PEG/PPG Dimethicone (Abil B8851 from Goldschmidt) | 0.5% |
| Cyclopentasiloxane (Dow Corning 245 Fluid) | 15.0% |
| Compound of Example 1 | 1.0% |
| Propylene glycol | 2.5% |
| Preserving agent | qs |
| Fragrance | qs |
| Citric acid/sodium hydroxide qs | pH 6.5 |
| Water qs | 100 |

Examples 5-7

Dye compositions were prepared using the following ingredients, the amounts of which are given as weight percentages of active material relative to the total weight of the composition:

| | Ex. 4 | Ex. 5 | Ex. 6 |
|---|---|---|---|
| para-Phenylenediamine | 0.24 | 0.24 | 0.24 |
| para-Aminophenol | 0.44 | 0.44 | 0.44 |
| 2-Aminophenol | 0.028 | 0.028 | 0.028 |
| 1,3-Dihydroxybenzene | 0.192 | 0.192 | 0.192 |
| 3-Aminophenol | 0.019 | 0.019 | 0.019 |
| 5-N-(β-Hydroxyethyl)amino-2-methylphenol | 0.021 | 0.021 | 0.021 |
| 1,3-Dihydroxy-2-methylbenzene | 0.055 | 0.055 | 0.055 |
| Anhydrous sodium metasilicate | 2 | 2 | 2 |
| Monoethanolamine | 5.45 | 5.45 | 5.45 |
| Reducing agent, antioxidant, sequestering agent, fragrance | qs | qs | qs |
| Propylene glycol | 10 | 10 | 10 |
| Crosslinked acrylic acid polymer | 0.4 | 0.4 | 0.4 |
| Compound of Example 1 | 1.5 | 1.5 | 2.8 |
| Cationic polymer: hexadimethrine chloride (CTFA name) Mexomer PO sold by the company Chimex | 3 | 3 | — |
| Powdered sodium lauryl sulfate | 3 | — | — |
| Lauryl alcohol oxyethylenated with 12 mol of ethylene oxide | — | 7.5 | 7.5 |
| Oleocetyl alcohol oxyethylenated with 30 mol of ethylene oxide | — | 4 | 4 |
| Decyl alcohol oxyethylenated with 3 mol of ethylene oxide | 10 | 10 | 10 |
| Decyl alcohol oxyethylenated with 5 mol of ethylene oxide | 8 | — | — |
| Lauric acid | 2.5 | 2.5 | 2.5 |
| 50/50 cetylstearyl alcohol | 11.5 | 11.5 | 11.5 |
| Nacreous agent: hydrophobic fumed silica | 1.2 | 1.2 | 1.2 |
| Nacreous agent: glyceryl monostearate | 2 | 2 | 2 |
| Demineralized water qs | 100 | 100 | 100 |

At the time of use, each dye composition described above was mixed weight-for-weight with a 20-volumes hydrogen peroxide solution (6% by weight).

The mixtures thus prepared were applied for 30 minutes to locks of natural or permanent-waved grey hair containing 90% white hairs. The locks were then rinsed, washed with a standard shampoo, rinsed again and then dried.

The hair was dyed in a golden-blond shade for each of the Examples 4 to 6.

Example 8

Another dye composition was prepared using the following ingredients, the amounts of which are given as weight percentages of active material relative to the total weight of the composition:

| | |
|---|---|
| Mixture of C18 to C24 linear alcohols | 3 |
| (C18/C20/C22/C24:7/57/30/6 - alcohol content >95%) | |
| Oxyethylenated stearyl alcohol (2 mol of ethylene oxide) | 4.5 |
| Oxyethylenated stearyl alcohol (21 mol of ethylene oxide) | 1.75 |
| Oleic acid | 2.6 |
| Cationic polyurethane obtained by condensation of 1,3-bis-(isocyanatomethylcyclohexane), N,N-dimethylethanolamine quaternized with bromododecane, N,N-dimethylethanolamine and polyoxyethylene of molecular weight 10 000 | 0.2 |
| Crosslinked poly(acrylic acid) (product sold under the name Carbopol 980 by the company Noveon) | 0.4 |
| Hydroxypropylmethylcellulose | 0.2 |
| Coconut acid monoisopropanolamide | 3 |
| Merquat 100 as an aqueous 40% solution | 1.6 |
| Compound of Example 1 | 2 |
| Sodium metabisulfite | 0.71 |
| EDTA (ethylenediaminetetraacetic acid) | 0.2 |
| tert-Butylhydroquinone | 0.3 |
| 1,4-Diaminobenzene | 0.2 |
| para-Aminophenol | 1.2 |
| 1,3-Dihydroxybenzene | 0.1 |
| 1-Hydroxy-3-aminobenzene | 0.2 |
| 1-Methyl-2-hydroxy-4-β-hydroxyethylaminobenzene | 0.8 |
| Monoethanolamine | 1 |
| Aqueous ammonia containing 20% $NH_3$ | 11 |
| Fragrance | qs |
| Demineralized water qs | 100 |

This composition is mixed at the time of use with an oxidizing composition in emulsion form containing as oxidizing agent 7.5% hydrogen peroxide, in a proportion of 1 part by weight of dye composition per 1.5 parts by weight of oxidizing composition. The mixture obtained is applied to locks of natural hair containing 90% white hairs, and is left to act for 30 minutes. After rinsing, washing with shampoo and drying, hair dyed in a strong coppery-red light-chestnut shade is obtained.

Example 9

The following compositions were prepared, the percentages indicated being weight percentages relative to the total weight of the composition:

Oxidizing Composition:

| | |
|---|---|
| Fatty alcohol | 2.3% |
| Oxyethylenated fatty alcohol | 0.6% |
| Fatty amide | 0.9% |
| Glycerol | 0.5% |
| Hydrogen peroxide | 7.5% |
| Fragrance | qs |
| Demineralized water qs | 100% |

Dye Composition:

| | |
|---|---|
| Mixture of C18 to C24 linear alcohols [C18/C20/C22/C24, 7/58/30/6, alcohol content >95%] (Nafol 20-22) | 3% |
| Mixture of C18 to C24 linear alcohols [C18/C20/C22/C24, 7/58/30/6, alcohol content >95%] in oxyethylenated form (30 mol of ethylene oxide) (Nafolox 20-22) | 1.35% |
| Oxyethylenated stearyl alcohol (2 mol of ethylene oxide) | 4% |
| Oxyethylenated stearyl alcohol (21 mol of ethylene oxide) | 2% |
| Oleic acid | 2.6% |
| Glycol distearate | 2% |
| Propylene glycol | 5% |
| Coconut acid monoisopropanolamide | 2% |
| Aculyn 44 sold by the company Rohm & Haas | 1.4% AM* |
| Crosslinked poly(acrylic acid) | 0.6% |
| Compound of Example 1 | 3% AM* |
| Merquat 100 sold by the company Calgon | 0.4% AM* |
| Reducing agents | 0.7% |
| Sequestering agents | 0.2% |
| 1,3-Dihydroxybenzene (resorcinol) | 0.6% |
| 1,4-Diaminobenzene | 0.5% |
| 1-Hydroxy-3-aminobenzene | 0.1% |
| 1-Hydroxy-2-aminobenzene | 0.05% |
| 1-Hydroxy-4-aminobenzene | 0.09% |
| 6-Hydroxybenzomorpholine | 0.017% |
| 1-β-Hydroxyethyloxy-2,4-diaminobenzene dihydrochloride | 0.039% |
| Propylene glycol monobutyl ether | 2.5% |
| Pure monoethanolamine | 1.06% |
| Aqueous ammonia (containing 20.5% ammonia) | 11.1% |
| Water qs | 100% |

AM* = Active Material

The dye composition was mixed, at the time of use, in a plastic bowl and for 2 minutes, with the oxidizing composition given above, in a proportion of 1 part of dye composition per 1.5 parts of oxidizing composition.

The mixture obtained was applied to locks of natural hair containing 90% white hairs, and was left to act for 30 minutes.

The locks were then rinsed with water, washed with shampoo, rinsed again with water and then dried and disentangled.

The hair was then dyed in a strong light-chestnut shade.

Example 10

Another dye composition was prepared using the following ingredients, the amounts of which are given as weight percentages of active material relative to the total weight of the composition:

| | |
|---|---|
| Oleocetyl alcohol oxyethylenated with 30 mol of ethylene oxide (nCA = 17 - HLB = 16.5) | 7% |
| Lauryl alcohol (C12-C14/55-45%) oxyethylenated with 12 mol of ethylene oxide (nCA = 12.5 - HLB = 14) | 8% |
| Cetylstearyl alcohol (C16/C18-50/50)(nCB = 17 - HLB = 1) | 5% |
| Decyl alcohol (C10-C12-C14/85-8.5-6.5) oxyethylenated with 3.5 mol of ethylene oxide, sold under the name Mergital BL 309 by the company Henkel (nCB = 10.4 - HLB = 8.5) | 22% |
| Copolymer of diallyldimethylammonium chloride and of acrylic acid, sold under the name Merquat 280 by the company Calgon, containing 35% AM | 3% AM |
| Compound of Example 1 | 1% |
| Crosslinked poly(acrylic acid) sold under the name Carbopol 934 (MW 3 000 000) by the company Goodrich | 0.4% |
| Propylene glycol | 8% |
| Monoethanolamine | 8.3% |
| Hydroquinone | 0.1% |
| 1-Phenyl-3-methyl-5-pyrazolone | 0.1% |
| Aqueous sodium bisulfite solution containing 35% AM | 1.3% |
| para-Phenylenediamine | 0.5% |

-continued

| | |
|---|---|
| m-Dihydroxybenzene | 0.4% |
| Fragrance, sequestering agent | qs |
| Eau qs | 100% |
| pH = 11.0 | |

AM: Active Material

The invention claimed is:

1. At least one grafted polysaccharide compound comprising at least one non-polymer siloxane graft, wherein the grafted polysaccharide compound is obtained by reacting at least one polysaccharide and at least one siloxane compound of formula (I):

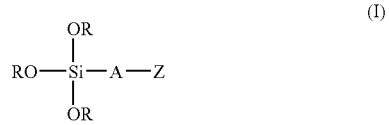
(I)

wherein:
R is independently chosen from linear and branched $C_1$-$C_{12}$ alkyl groups and linear and branched $C_2$-$C_8$ alkenyl groups;
A is chosen from linear or branched $C_1$-$C_6$ alkylene groups and linear or branched $C_2$-$C_8$ alkenylene groups, and optionally comprising in the chain, a heteroatom chosen from nitrogen, oxygen, and sulfur atoms, and wherein the alkylene and alkenylene groups optionally comprise at least one hydroxyl substituent;
Z is chosen from —$NHR_4$, —$^+NR_1R_2R_3X^-$, —C≡N, —SH, —OH, guanidine, guanidinium salts, sulfonate salts, sulfate salts, phosphate salts, and phosphonate salts, wherein the salts may be chosen from organic and mineral salts;
$R_4$ is chosen from a hydrogen atom and linear and branched $C_1$-$C_{22}$ alkyl groups, optionally comprising at least one hydroxyl and/or quaternary ammonium substituent;
$R_1$, $R_2$, and $R_3$ are each independently chosen from a hydrogen atom and linear or branched $C_1$-$C_{22}$ alkyl groups, optionally comprising at least one hydroxyl substituent; and
X is chosen from mineral and organic anions;
and wherein the at least one polysaccharide is chosen from a hemicellulose, a lignocellulose, a starch, an inulin, a guar gum, a xanthan gum, a pullulan, an agar-agar, a sodium, potassium or ammonium alginate, a carrageenan, a dextran, a furcellaran, a gellan gum, a gum arabic, a gum tragacanth, a hyaluronic acid, a konjac mannan, a lignin sulfonate, a carob gum, a partially N-acetylated chitin, a pectin, a polydextrose, a rhamsan gum, and a welan gum.

2. The grafted polysaccharide compound according to claim 1, wherein R of the at least one siloxane compound is independently chosen from methyl, ethyl, n-propyl, isopropyl, n-butyl, tert-butyl, vinyl, allyl, crotonyl, butenyl, isobutenyl, and tert-butenyl groups.

3. The grafted polysaccharide compound according to claim 1, wherein A of the at least one siloxane compound is chosen from methylene, ethylene, n-propylene, isopropylene, n-butylene, tert-butylene, hexylene, octylene, vinylene, allylene, crotonylene, butenylene, isobutenylene, tert-butenylene, hexenylene, and octenylene groups, optionally comprising in the chain, a heteroatom chosen from nitrogen, oxygen, and sulfur atoms, and wherein the siloxane optionally comprises at least one hydroxyl substituent.

4. The grafted polysaccharide compound according to claim 1, wherein $R_1$, $R_2$, $R_3$, and $R_4$ of the at least one siloxane compound are independently chosen from linear and branched $C_1$-$C_4$ alkyl groups, and linear and branched $C_{12}$-$C_{18}$ alkyl groups.

5. The grafted polysaccharide compound according to claim 4, wherein $R_1$, $R_2$, $R_3$, and $R_4$ of the at least one siloxane compound are independently chosen from methyl, ethyl, n-propyl, isopropyl, n-butyl, tert-butyl, lauryl, myristyl, cetyl, and stearyl groups.

6. The grafted polysaccharide compound according to claim 1, wherein X of the at least one siloxane compound is chosen from halogen atoms, acetate, citrate, lactate, oleate, and behenate.

7. The grafted polysaccharide compound according to claim 1, wherein the at least one polysaccharide has a weight-average molecular mass ranging from 500 to 15,000,000.

8. A cosmetic composition comprising, in a cosmetically acceptable medium, at least one grafted polysaccharide compound comprising at least one non-polymer siloxane graft, wherein the at least one grafted polysaccharide compound is obtained by reacting at least one polysaccharide and at least one siloxane compound of formula (I):

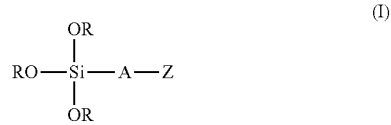
(I)

wherein:
R is independently chosen from linear and branched $C_1$-$C_{12}$ alkyl groups and linear and branched $C_2$-$C_8$ alkenyl groups;
A is chosen from linear and branched, saturated and unsaturated, optionally hydroxylated $C_1$-$C_{22}$ divalent hydrocarbon-based groups, optionally comprising a heteroatom in the chain, chosen from nitrogen, oxygen, and sulfur atoms;
Z is chosen from —$NHR_4$, —$^+NR_1R_2R_3X^-$, —C≡N, —SH, —OH, guanidine, guanidinium salts, sulfonate salts, sulfate salts, phosphate salts, and phosphonate salts, wherein the salts may be chosen from organic and mineral salts;
$R_4$ is chosen from a hydrogen atom and linear and branched $C_1$-$C_{22}$ alkyl groups, optionally comprising at least one hydroxyl and/or quaternary ammonium substituent;
$R_1$, $R_2$, and $R_3$ are each independently chosen from a hydrogen atom and linear and branched $C_1$-$C_{22}$ alkyl groups, optionally comprising at least one hydroxyl substituent; and
X is chosen from mineral and organic anions; and
wherein the cosmetically acceptable medium comprises water or a mixture of water and at least one organic solvent chosen from $C_1$-$C_4$ lower alcohols, alkylene polyols, and polyol ethers, and
wherein the cosmetic composition further comprises at least one additive chosen from anionic, cationic, nonionic, amphoteric and zwitterionic surfactants; anionic, cationic, nonionic, amphoteric and zwitterionic polymers; thickeners; nacreous agents; opacifiers; UV-screening agents; fragrances; mineral, plant and synthetic oils; fatty acid esters; dyes; volatile or nonvolatile, organomodified or non-organomodified, cyclic or acyclic, branched or unbranched silicones; mineral, organic, natural or synthetic particles; preserving agents; and pH stabilizers.

9. The cosmetic composition according to claim 8, wherein the at least one grafted polysaccharide compound is present in an amount ranging from 0.05% to 50% by weight relative to the total weight of the composition.

10. The cosmetic composition according to claim 9, wherein the at least one grafted polysaccharide compound is present in an amount ranging from 0.5% to 25% by weight, relative to the total weight of the composition.

11. A method for treating keratin materials, comprising applying to the keratin materials, a cosmetic composition comprising, in a cosmetically acceptable medium, at least one grafted polysaccharide compound comprising at least one non-polymer siloxane graft, wherein the at least one grafted polysaccharide compound is obtained by reacting at least one polysaccharide and at least one siloxane compound of formula (I):

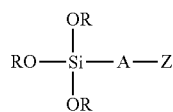
(I)

wherein:
R is independently chosen from linear and branched $C_1$-$C_{12}$ alkyl groups and linear and branched $C_2$-$C_8$ alkenyl groups;
A is chosen from linear and branched, saturated and unsaturated, optionally hydroxylated $C_1$-$C_{22}$ divalent hydrocarbon-based groups, optionally comprising a heteroatom in the chain, chosen from nitrogen, oxygen, and sulfur atoms;
Z is chosen from —$NHR_4$, —$^+NR_1R_2R_3X^-$, —C≡N, —SH, —OH, guanidine, guanidinium salts, sulfonate salts, sulfate salts, phosphate salts, and phosphonate salts, wherein the salts may be chosen from organic and mineral salts;
$R_4$ is chosen from a hydrogen atom and linear and branched $C_1$-$C_{22}$ alkyl groups, optionally comprising at least one hydroxyl and/or quaternary ammonium substituent;
$R_1$, $R_2$, and $R_3$, are each independently chosen from a hydrogen atom and linear and branched $C_1$-$C_{22}$ alkyl groups, optionally comprising at least one hydroxyl substituent; and
X is chosen from mineral and organic anions.

12. The method according to claim 11, wherein the at least one polysaccharide is a polysaccharide chain chosen from hemicellulose, lignocellulose, starch, inulin, guar gum, xanthan gum, pullulan, agar-agar, sodium alginate, potassium alginate, ammonium alginate, carrageenan, dextran, furcellaran, gellan gum, gum arabic, gum tragacanth, haluronic acid, konjac mannan, lignin sulfonate, carob gum, partially N-acetylated chitin, pectin, polydextrose, rhamsan gum, and welan gum.

13. The method according to claim 11, wherein the at least one polysaccharide has a weight-average molecular mass ranging from 500 to 15,000,000.

14. The method according to claim 11, wherein the at least one polysaccharide is chosen from cellulose, hemicellulose, carboxymethylcellulose, hydroxyethylcellulose, hydroxypropylcellulose, hydroxypropylmethylcellulose, methylcellulose, lignocellulose, starch, starch acetate, hydroxyethyl starch, hydroxypropyl starch, inulin, guar gum, carboxymethyl guar gum, carboxymethylhydroxylpropyl guar gum, hydroxyethyl guar gum, hydroxypropyl guar gum, and xanthan gum.

15. The cosmetic composition according to claim 8, wherein the at least one polysaccharide is a polysaccharide chain chosen from hemicellulose, lignocellulose, starch, inulin, guar gum, xanthan gum, pullulan, agar-agar, sodium alginate, potassium alginate, ammonium alginate, carrageenan, dextran, furcellaran, gellan gum, gum arabic, gum tragacanth, haluronic acid, konjac mannan, lignin sulfonate, carob gum, partially N-acetylated chitin, pectin, polydextrose, rhamsan gum, and welan gum.

16. The cosmetic composition according to claim 8, wherein the at least one polysaccharide has a weight-average molecular mass ranging from 500 to 15,000,000.

17. The cosmetic composition according to claim 8, wherein the at least one polysaccharide is a polysaccharide chain chosen from cellulose, hemicellulose, carboxymethylcellulose, hydroxyethylcellulose, hydroxypropylcellulose, hydroxypropylmethylcellulose, methylcellulose, lignocellulose, starch, starch acetate, hydroxyethyl starch, hydroxypropyl starch, inulin, guar gum, carboxymethyl guar gum, carboxymethylhydroxylpropyl guar gum, hydroxyethyl guar gum, hydroxypropyl guar gum, and xanthan gum.

18. At least one grafted polysaccharide compound comprising at least one non-polymer siloxane graft, wherein the grafted polysaccharide compound is obtained by reacting at least one polysaccharide and at least one siloxane compound of formula (I):

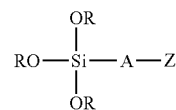
(I)

wherein:
R is independently chosen from linear and branched $C_1$-$C_{12}$ alkyl groups and linear and branched $C_2$-$C_8$ alkenyl groups;
A is chosen from linear or branched $C_1$-$C_6$ alkylene groups and linear or branched $C_2$-$C_8$ alkenylene groups, and optionally comprising in the chain, a heteroatom chosen from nitrogen, oxygen, and sulfur atoms, and wherein the alkylene and alkenylene groups optionally comprise at least one hydroxyl substituent;
Z is chosen from —$NHR_4$, —$^+NR_1R_2R_3X^-$, —C≡N, —SH, —OH, guanidine, guanidinium salts, sulfonate salts, sulfate salts, phosphate salts, and phosphonate salts, wherein the salts may be chosen from organic and mineral salts;
$R_4$ is chosen from a hydrogen atom and linear and branched $C_1$-$C_{22}$ alkyl groups, optionally comprising at least one hydroxyl and/or quaternary ammonium substituent;
$R_1$, $R_2$, and $R_3$ are each independently chosen from a hydrogen atom and linear or branched $C_1$-$C_{22}$ alkyl groups, optionally comprising at least one hydroxyl substituent; and
X is chosen from mineral and organic anions;
and wherein the at least one polysaccharide is chosen from hemicellulose, carboxymethylcellulose, hydroxyethylcellulose, hydroxypropylcellulose, hydroxypropylmethylcellulose, methylcellulose, lignocellulose, starch, starch acetate, hydroxyethyl starch, hydroxypropyl starch, inulin, guar gum, carboxymethyl guar gum, carboxymethylhydroxylpropyl guar gum, hydroxyethyl guar gum, hydroxypropyl guar gum, and xanthan gum.

* * * * *